(12) United States Patent
Konishi et al.

(10) Patent No.: US 9,713,426 B2
(45) Date of Patent: Jul. 25, 2017

(54) BLOOD SAMPLING DEVICE

(75) Inventors: Satoshi Konishi, Shiga (JP); Taizo Kobayashi, Shiga (JP); Hiroshi Yoshida, Osaka (JP); Takashi Wada, Hyogo (JP); Fumihiro Hagiwara, Hyogo (JP); Norihide Takeyama, Tokyo (JP)

(73) Assignee: Nipro Corporation (JP)

( * ) Notice: Subject to any disclaimer, the term of this patent is extended or adjusted under 35 U.S.C. 154(b) by 0 days.

(21) Appl. No.: 13/637,221

(22) PCT Filed: Mar. 25, 2011

(86) PCT No.: PCT/JP2011/057410
§ 371 (c)(1),
(2), (4) Date: Nov. 28, 2012

(87) PCT Pub. No.: WO2011/122484
PCT Pub. Date: Oct. 6, 2011

(65) Prior Publication Data
US 2013/0231572 A1    Sep. 5, 2013

(30) Foreign Application Priority Data
Mar. 27, 2010    (JP) .................................. 2010-073947

(51) Int. Cl.
*A61B 5/153*    (2006.01)
*A61B 5/00*    (2006.01)
(Continued)

(52) U.S. Cl.
CPC ........ *A61B 5/0082* (2013.01); *A61B 5/15003* (2013.01); *A61B 5/153* (2013.01);
(Continued)

(58) Field of Classification Search
CPC ..... A61B 5/489; A61B 5/0059; A61B 5/1455; A61B 5/72; A61B 2017/00057; A61B 5/0095; A61B 1/0638
(Continued)

(56) References Cited

U.S. PATENT DOCUMENTS 6,093,172 A * 7/2000 Funderburk .......... A61M 5/158
604/131
6,249,713 B1 * 6/2001 Geiger ............... A61B 17/3403
378/42
(Continued)

FOREIGN PATENT DOCUMENTS

JP    2006-102110    4/2006
JP    2006-102360    4/2006
(Continued)

*Primary Examiner* — Vani Gupta
(74) *Attorney, Agent, or Firm* — ;Jordan and Koda, PLLC

(57) ABSTRACT

The position of blood vessels can be more appropriately specified by means of appropriately selecting, on the basis of the conditions and components utilized, and angle between a light emitting unit optical axis of a near-infrared light emitting unit and a normal light of an irradiated surface, and angle between an optical axis of a light receiving side lens and the normal line of the irradiated surface, and an angle between a light receiving surface of a photo diode array and the light receiving unit optical axis. Thus, the subcutaneous blood vessel depth in the direction of the normal line from the irradiated surface can be specified based on changes in illumination intensity in a photodiode array. Consequently, the position of subcutaneous blood vessels can be easily specified.

10 Claims, 12 Drawing Sheets

(51) Int. Cl.
- *A61B 5/15* (2006.01)
- *A61B 1/06* (2006.01)
- *A61B 5/1455* (2006.01)
- *A61B 17/00* (2006.01)
- *A61M 5/42* (2006.01)

(52) U.S. Cl.
CPC .. *A61B 5/150175* (2013.01); *A61B 5/150267* (2013.01); *A61B 5/150389* (2013.01); *A61B 5/489* (2013.01); *A61B 1/0638* (2013.01); *A61B 5/0059* (2013.01); *A61B 5/0095* (2013.01); *A61B 5/1455* (2013.01); *A61B 5/150748* (2013.01); *A61B 5/72* (2013.01); *A61B 2017/00057* (2013.01); *A61M 5/427* (2013.01)

(58) Field of Classification Search
USPC .................................................... 600/473
See application file for complete search history.

(56) References Cited

U.S. PATENT DOCUMENTS

| | | | | |
|---|---|---|---|---|
| 6,665,554 | B1* | 12/2003 | Charles | A61B 34/70 600/427 |
| 2005/0281445 | A1* | 12/2005 | Marcotte | 382/128 |
| 2006/0100523 | A1* | 5/2006 | Ogle | A61B 5/0059 600/473 |
| 2006/0270919 | A1* | 11/2006 | Brenner | 600/310 |
| 2007/0239033 | A1* | 10/2007 | Tearney et al. | 600/476 |
| 2009/0147998 | A1* | 6/2009 | Yamaguchi | A61B 1/00009 382/106 |
| 2010/0067015 | A1* | 3/2010 | Matsushita | G01J 3/02 356/445 |

FOREIGN PATENT DOCUMENTS

| | | |
|---|---|---|
| JP | 2007-125324 | 5/2007 |
| JP | 2009-064455 | 3/2009 |

* cited by examiner

BLOOD SAMPLING DEVICE

BACKGROUND OF THE INVENTION

The present invention relates to a blood sampling device which samples blood from subcutaneous blood vessels, and particularly relates to one which specifies the position of blood vessels using near-infrared rays.

A blood vessel position presenting apparatus which is one of former blood position specifying devices is described with reference to FIG. 11. The blood vessel position presenting apparatus is a device capable of confirming the position and the direction of blood vessels.

The blood vessel position presenting apparatus of FIG. 11 is constituted including an image pick-up unit 101, an image processing unit 102, an illuminating unit 103, a display unit 104, a mark control unit 105, and a mark illuminating unit 106.

The illuminating unit 103 irradiates a living body with a near-infrared illumination light beam 127 which is an illumination light beam of a near-infrared wavelength region and is constituted including a near-infrared LED.

The image pick-up unit 101 takes a photograph of a living body and is, for example, a monochrome CCD camera or a monochrome CMOS camera having high spectral sensitivity from visible wavelength to near infrared wavelength region. The image pick-up information obtained from a reflected light beam 129 from a living body is transferred to the image processing unit 102 as a living body image information 121. The image pick-up unit 101 obtains a near-infrared image information which is living body image information when emitting the illumination light beam and a non-light image information which a living body image information when not emitting the illumination light beam, and then transfers the same to the image processing unit.

The display unit 104 displays an image based on an image information 124 output from the image processing unit 102 with a liquid crystal display or the like.

The mark illuminating unit 106 emits a puncture mark projecting light beam 128 for projecting a puncture mark showing a puncture position to the surface of a living body and is constituted including a visible light laser. The mark illuminating unit 106 emits the puncture mark projecting light beam 128 at an illumination timing and in an illumination direction based on a drive signal 126 from the mark control unit 105.

The mark control unit 105 generates the drive signal 126 based on a instruction signal 122 from the image processing unit 102. The instruction signal 122 contains a deviation information of the display position of the puncture mark included in an image displayed on the display unit 104 and the target position of the puncture mark input from the outside. The mark control unit 105 generates the drive signal 126 for matching the display position of the puncture mark with the target position of the puncture mark utilizing this deviation information.

The image processing unit 102 generates a processed near-infrared image information in which a blood vessel image and an injection needle image are emphasized based on the near-infrared image information which is a living body image information when emitting an illumination light beam, and generates a processed non-light image information in which a puncture mark image is emphasized based on the non-light image information which is a living body image information when not emitting an illumination light beam. Then, the processed near-infrared image information and the processed non-light image information are synthesized to obtain a display image information.

The elements illustrated in FIG. 11 are stored in a predetermined case, and are disposed at a predetermined positional relationship with a living body whose blood vessel position is to be detected for use.

FIG. 12 illustrates a general view of an example of the blood vessel position presenting apparatus. FIG. 12 illustrates an example in which the blood vessel position presenting apparatus and a living body are not fixed, and a case 202 is supported by scaffolds 209 and 210. The scaffolds 209 and 210 stabilize the case 202 and an arm 201 whose blood vessel position is to be detected in a state where the case 202 and the arm 201 are separated at a predetermined interval and the apparatus is disposed in such a manner that the case 202 and the scaffolds 209 and 210 surround the arm 201.

The case 202 is provided, on the upper surface, with a liquid crystal display portion 203 constituting the display unit 104, a trackball 204 which moves a cursor 207 displayed on the liquid crystal display portion 203, and an input button 208 for setting the position, of the cursor 207 as a target position of a puncture mark. On the liquid crystal display portion 203 of FIG. 2, blood vessels 206 and the cursor 207 are displayed. Onto the surface of the arm 201, a puncture mark 205 in the shape of a spot is projected.

When using the blood vessel position presenting apparatus of FIG. 12, a doctor and a nurse move the cursor 207 for setting the target position of the puncture mark using the trackball 204 on the screen of the liquid crystal display portion 203, and then pushing the input button 208 to thereby fix the position, indicated by the cursor 207 as the target position of the puncture mark. The puncture mark 205 is a mark projected by the mark illuminating unit 106, and looks red to the naked eye. The puncture mark 205 indicates an arbitrary portion on the surface of the arm 201 in the initial state. When the target position is fixed by the cursor 207, a red visible light laser of the mark illuminating unit 106 changes the direction in such a manner that the position of the puncture mark 205 and the target, position (the position of the cursor at this time) are matched on an image taken by the image pick-up unit 101.

The image processing unit 102 receives the near-infrared image information obtained when the illumination unit 103 emits a near-infrared light beam and the non-light image information obtained when the illumination unit 103 does not emit a light beam as a living body image information 121 from the image pick-up unit 101. As an example, the two kinds of image information are alternately input in time division. Since the venous blood has high absorptivity of a near-infrared light beam, a blood vessel portion appears in black and an injection needle appears in white on the image based on the near-infrared image information. On an image based on the non-light image information, the puncture mark projected onto the arm 201 by a puncture mark projecting light beam 128 which is a visible light beam appears.

CITATION LIST

[Patent Document 1] Japanese Unexamined Patent Application Publication No. 2006-102110

SUMMARY OF THE INVENTION

The above-described blood vessel position presenting apparatus needs to be improved as described below. In the blood vessel position presenting apparatus, the image processing unit 102 synthesizes a processed near-infrared image information and a processed non-light image information to generate a display image information. Moreover, the image processing unit 102 generates a processed near-infrared image information in which a blood vessel image and an injection needle image are emphasized based on the near-infrared image information. Furthermore, the image processing unit 102 generates a processed non-light image information in which an image of a puncture mark is emphasized based on non-light image information.

Thus, the former blood vessel position presenting apparatus presents a blood vessel position by processing a predetermined image information. Therefore, an image processing unit having high processing capability is required.

In order to treat image information, a display unit 104, such as a liquid crystal display for displaying the image information, is required. Furthermore, a mark illuminating unit 106 is required which emits a puncture mark projecting light beam 123 for projecting a puncture mark for indicating a puncture position on the surface of a living body.

Thus, since the former blood vessel position presenting apparatus requires a large number of components, the device itself becomes large. Thus, the device needs to be improved in that and it is difficult to use the device regardless of time or place, for example during going out.

Moreover, since the former blood vessel position presenting apparatus requires a large number of components and also requires expensive components, the device needs to be improved in that the device is difficult for an individual to own.

Then, the present invention aims at providing a blood vessel position specifying device capable of easily specifying the position of blood vessels.

Means for solving the problems to be solved in the invention and the effects of the invention are described below.

The blood vessel position specifying device according to the invention is a blood vessel position specifying device which specifies the position of blood vessels present under the skin. The blood vessel position specifying device has: a light projection unit which has a light projection axis having a predetermined angle to the normal line of a predetermined irradiated surface and which projects a near-infrared ray toward the intersection of the light projection axis and the normal line; a spectral lens which is located at the same side as the side where the light projection unit is located relative to the irradiated surface, which receives the reflected light beam of the near-infrared ray projected by the light projection unit, which disperses the reflected light beam, and which, has an optical axis having a predetermined angle to the normal line of the irradiated surface; a light receiving unit having a light receiving surface which receives the dispersed reflected light beam; and a blood vessel position calculation unit which calculates the position of the blood vessel based on the brightness of the reflected light beam on the light receiving surface, in which the intersection of the light projection axis and the optical axis of the spectral lens is located at the side opposite to the side where the light projection unit and the spectral lens are located relative to the irradiated surface.

When near-infrared rays are projected to the skin, the near-infrared rays are absorbed, at a position where a blood vessel is present under the skin, by the blood vessel. In contrast, at a position where a blood vessel is not present, the rays are diffused on the skin surface and in the skin, and some rays become reflected light beams heading to the outside of the skin. Therefore, by receiving the reflected light beams of the near-infrared rays projected to the skin, and then dispersing the same relative to the normal line direction of the irradiated surface to analyze a change in the brightness of the reflected light beams, the position of the blood vessel can be specified.

Thus, the blood vessel position specifying device according to the invention can easily specify the position of a blood vessel based on the change in the brightness of reflected light beams of near-infrared light beams.

In the blood vessel position specifying device according to the invention, the light receiving unit is disposed in such a manner that the light receiving surface inclines to the optical axis.

Thus, the image formation position at the light receiving surface of the dispersed reflected light beams can be changed according to the depth in the normal line direction of the irradiated surface. Therefore, the blood vessel position specifying device according to the invention can easily specify the position of blood vessels based on a change in the brightness of the reflected light beams of near-infrared light beams.

In the blood vessel position specifying device according to the invention, the light projection axis of the light projection unit and the optical axis of the spectral lens are present in the same plane.

Thus, the position of a blood vessel present in parallel to the plane where the light projection axis of the light projection unit and the optical axis of the spectral lens are present can be specified with good accuracy, In the blood vessel position specifying device according to the invention, the plane including the light projection axis of the light projection unit and the normal line of the irradiated surface and the plane including the optical axis of the spectral lens and the normal line of the irradiated surface are disposed at a predetermined angle.

Thus, the position of a blood vessel present at a predetermined angle to the plane where the light projection axis of the light projection unit and the optical axis of the spectral lens are present can be specified with good accuracy.

In the blood vessel position specifying device according to the invention, the plane including the light projection axis of the light projection unit and the normal line of the irradiated surface and the plane including the optical axis of the spectral lens and the normal line of the irradiated surface are disposed at 90°.

Thus, the position of a blood vessel, present at 90° to the plane where the light projection axis of the light projection unit and the optical axis of the spectral lens are present can be specified with good accuracy. By disposing the plane including the light projection axis of the light projection unit and the normal line of the irradiated surface in such a manner as to be orthogonal to each other, the position of blood vessels from a blood vessel present in parallel to the plane where the light projection axis of the light projection unit and the optical axis of the spectral lens are present to a blood vessel present sit 90° to the plane where the light projection axis of the light projection unit and the optical axis of the spectral lens are present can be specified with good accuracy.

In the blood vessel position specifying device according to the invention, the spectral lens is an aspherical lens. Thus, reflected light beams can be dispersed with good accuracy.

A blood sampling device according to the invention is a blood sampling device which samples blood from a blood vessel present under the skin and has the blood vessel position specifying device according to any one of Claim 1 to Claim 6 and a needle projecting unit having a needle for use in blood sampling and projecting the needle to the calculated blood vessel position.

Thus, a user can certainly and easily sample blood without failing in sampling of blood.

DESCRIPTION OF THE PREFERRED EMBODIMENTS

Hereinafter, embodiments of the invention are described in detail with reference to the drawings.

Embodiment 1

1. Configuration of Blood Sampling Device 100

Figure 1:
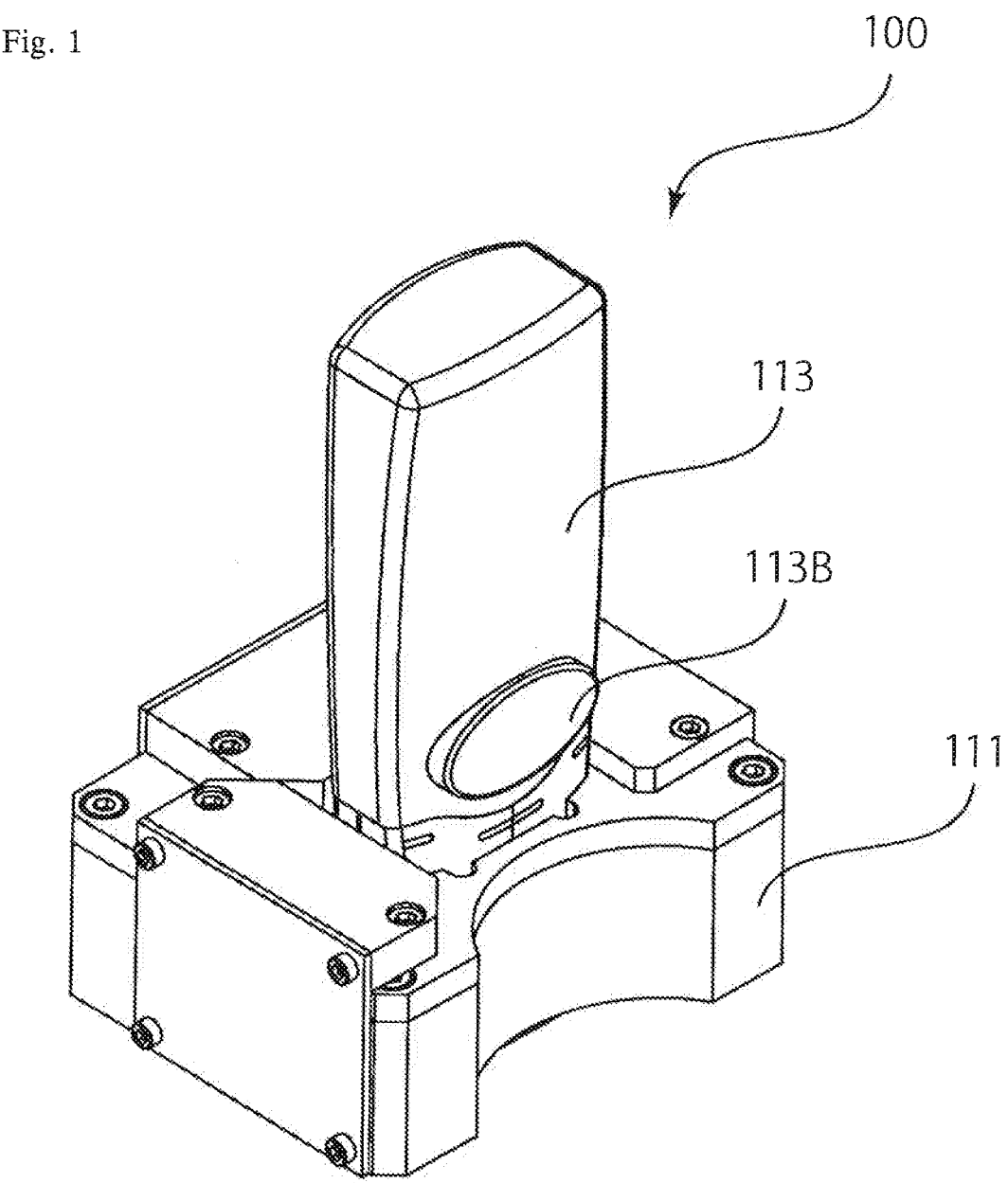
FIG. 1 is an outside view of a blood sampling device 100 containing a blood vessel position specifying device 111 according to the invention.

A blood sampling device 100 according to the invention is described with reference to FIG. 1. FIG. 1 illustrates a perspective view of the blood sampling device 100 as viewed from an obliquely upper side. The blood sampling device 100 has a blood vessel position specifying device 111 and a puncture device 113. The puncture device 113 is a device which inserts an injection needle into a blood vessel from the outside of the body to sample blood. The blood vessel position specifying device 111 is a device which specifies the position of a blood vessel from which blood is sampled.

The puncture device 113 can be attached to and detached from the blood vessel position specifying device 111. The puncture device 113 has a puncture needle 113b (FIG. 2) therein. The puncture device 113 is provided with a puncture button B113 at the side surface. The puncture device 113 projects the puncture needle 113b disposed inside to the outside when the puncture button B113 is pushed.

Figure 2:
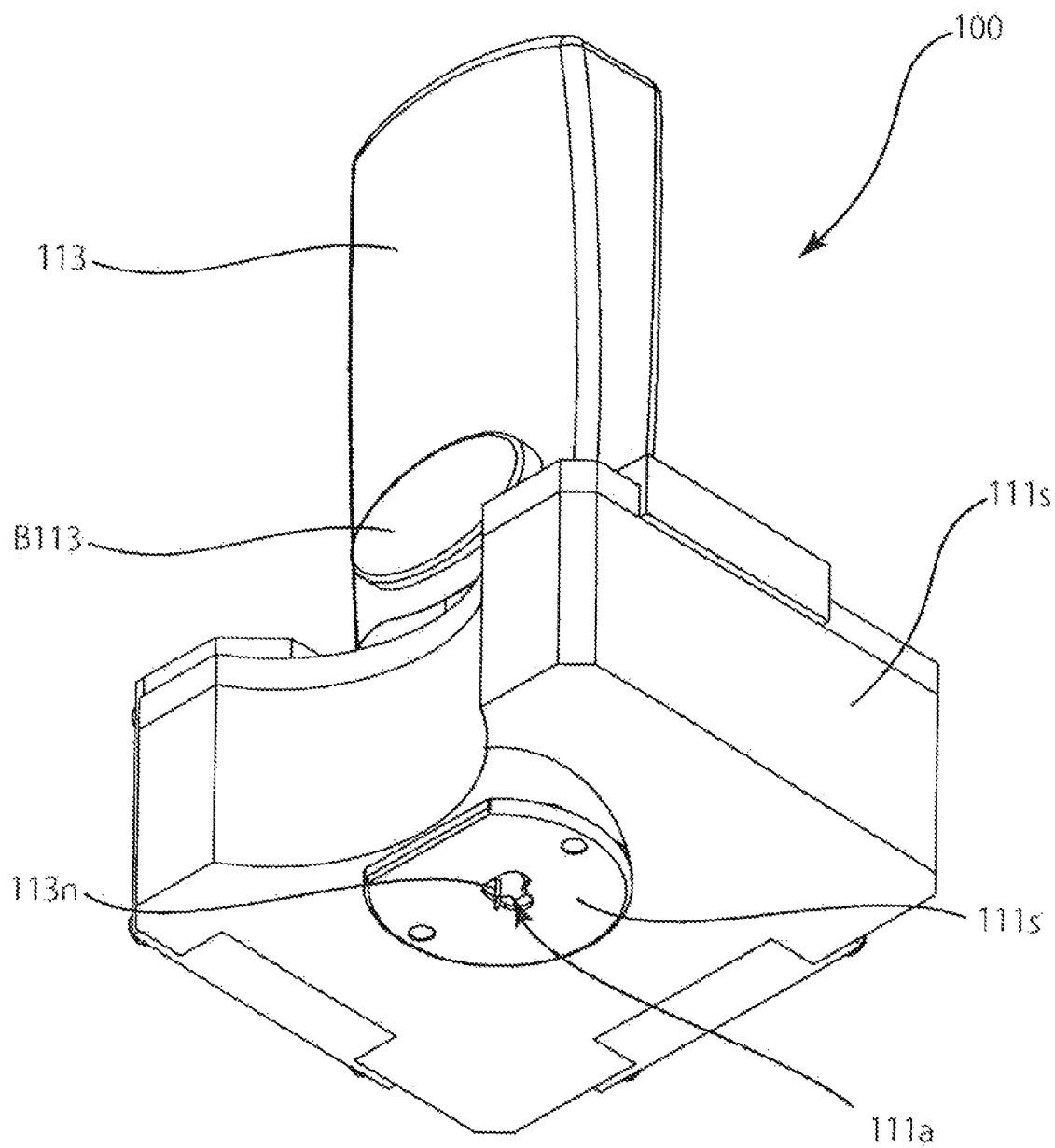
FIG. 2 is an outside view of the blood sampling device 100 containing the Hood vessel position specifying device 111 according to the invention.

FIG. 2 illustrates a perspective view of the blood sampling device 100 as viewed from an obliquely lower side. In the blood sampling device 100, the blood vessel position specifying device 111 has a puncture aperture 111a and a close contact surface 111s at the bottom. The close contact surface 111s is disposed around the puncture aperture 111a. The puncture needle 113b of the puncture device 113 is projected to the outside from the puncture aperture 111a.

A user of the blood sampling device 100 attaches the puncture device 113 to the blood vessel position specifying device 111. The user disposes the puncture device 113 in such a manner that the skin from which blood is to be sampled is brought into close contact with the close contact surface 111s. At this time, an irradiated surface is formed by the skin located at the position of the puncture aperture 111a of the blood vessel position specifying device 111.

After disposing the blood vessel position specifying device 111, the puncture button B113 is pushed. Thus, the puncture needle 113b is projected from the tip of the puncture device 113 to be inserted into the body.

3. Configuration of Blood Vessel Position Specifying Device 111

Figure 3:
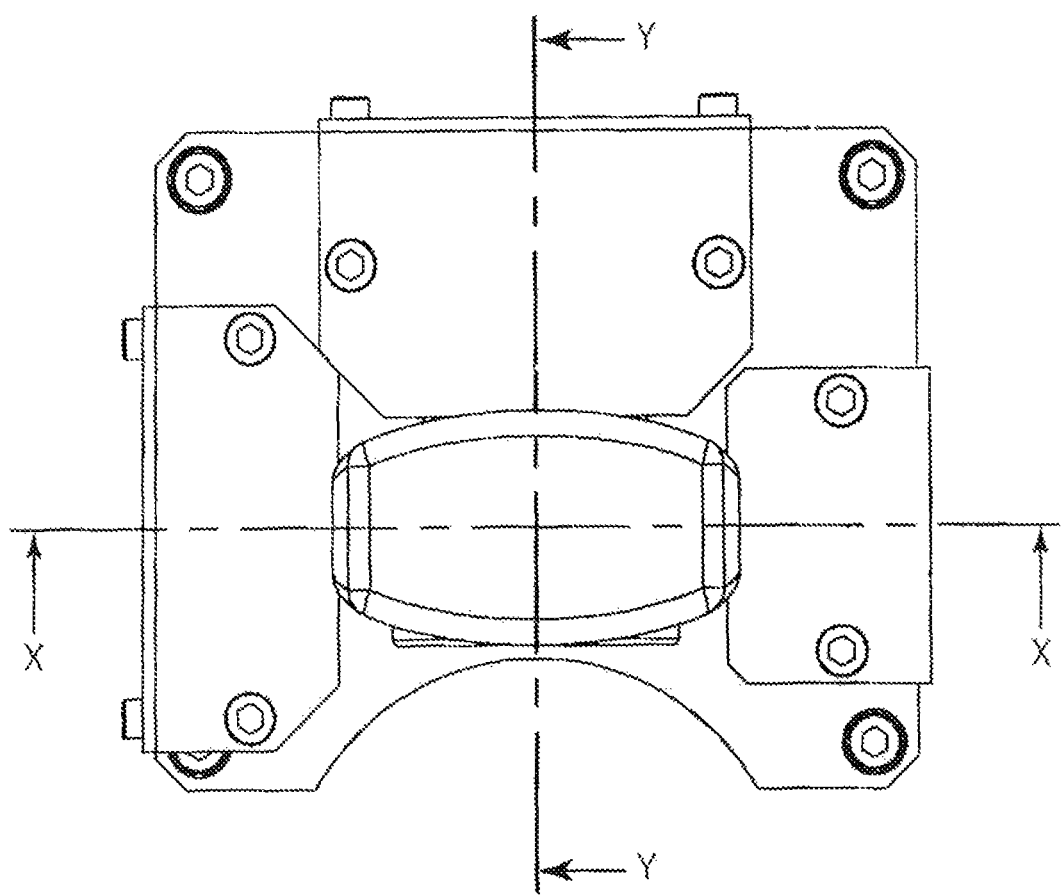
FIG. 3 is an upper surface view of the blood sampling device 100.
Figure 4:
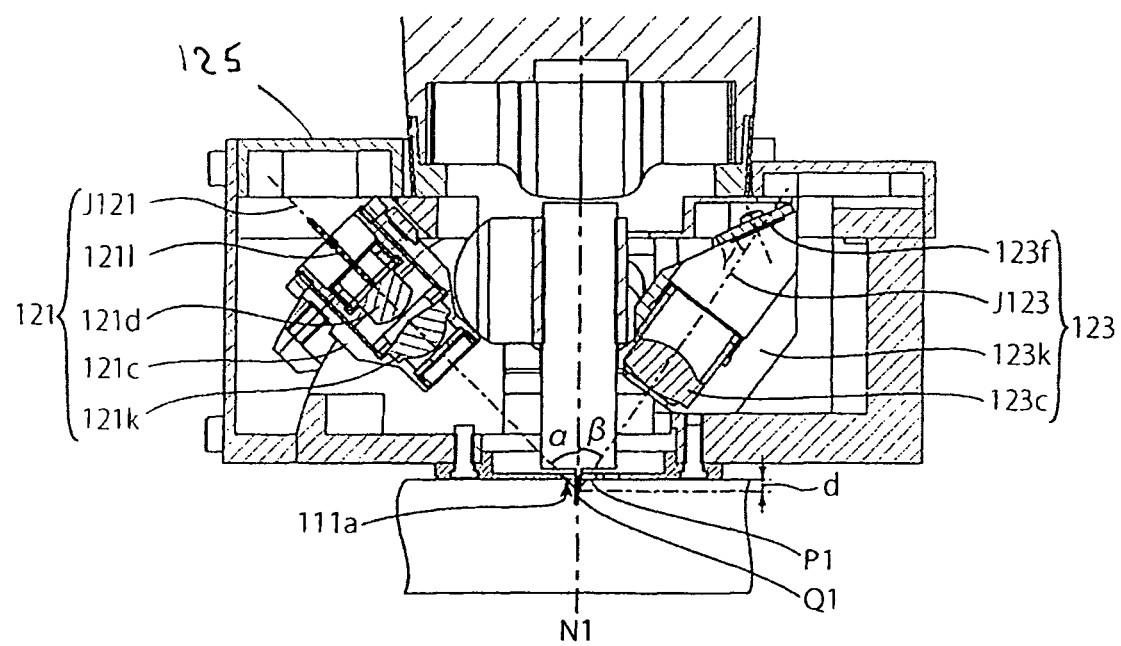
FIG. 4 is a cross sectional view of the XX cross section in FIG. 3.
Figure 5:
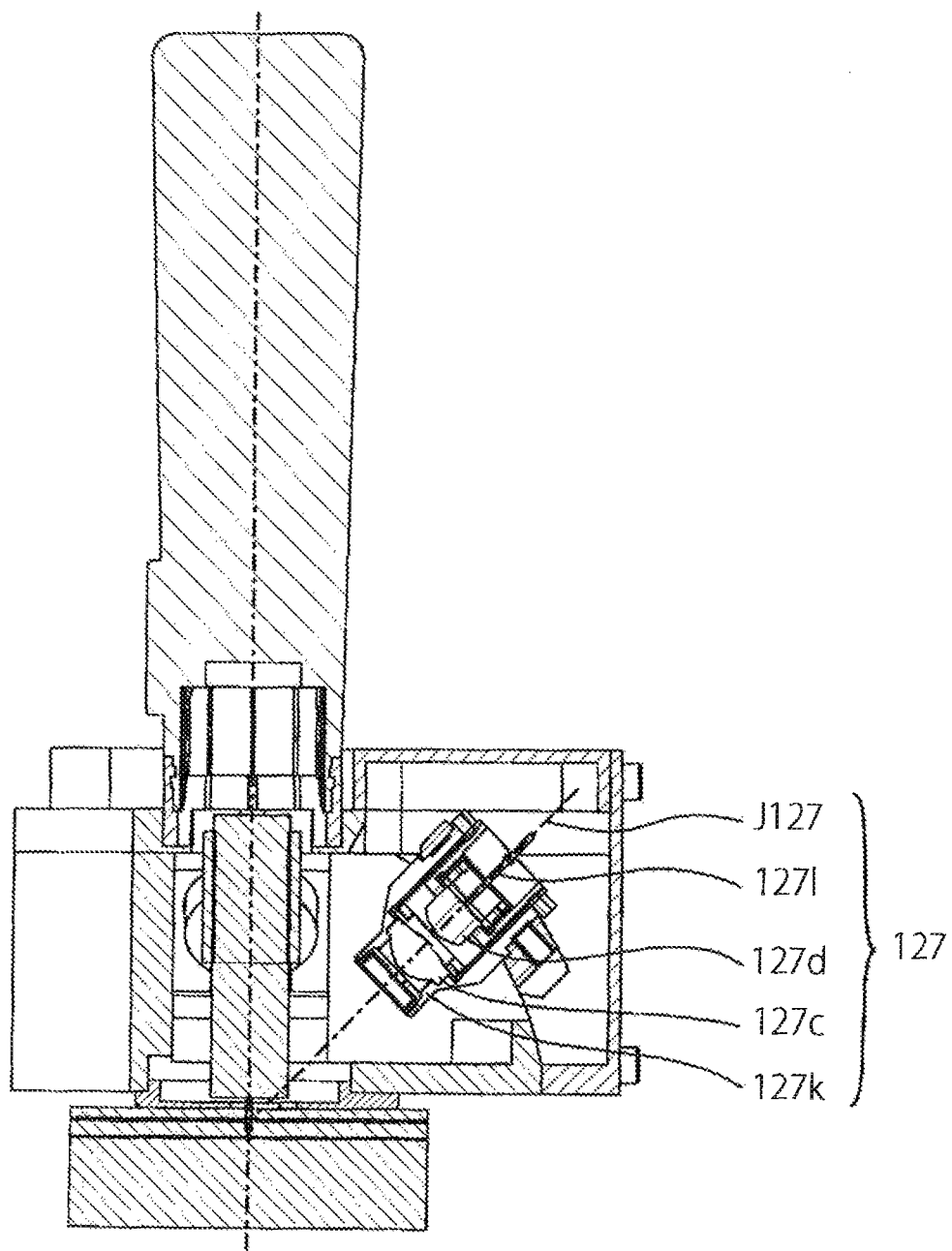
FIG. 5 is a cross sectional view of the YY cross section in FIG. 3.

The configuration of the blood vessel position specifying device 111 is described with reference to FIGS. 3, 4, and 5. FIG. 3 illustrates the top view of the blood sampling device 100. FIG. 4 illustrates the X-X cross section of the blood sampling device 100 illustrated in FIG. 3 and FIG. 5 illustrates the Y-Y cross section thereof. FIGS. 4 and 5 illustrate a state where the blood sampling device 100 is disposed at a predetermined position of a target person. FIG. 4 also illustrates a partial cross sectional view of the blood sampling device 100.

As illustrated in FIG. 4, the blood vessel position specifying device 111 has a near-infrared light emitting unit 121, a reflected light receiving unit 123, and a case 125. The near-infrared light emitting unit 121 and the reflected light receiving unit 123 are attached to predetermined positions of the case 125.

The near-infrared light emitting unit 121 has a near-infrared light emitting diode 121d, a light emission side lens 121c, and a case 121k. The near-infrared light emitting unit 121 has an optical axis J121 (hereinafter referred to as a light emitting unit optical axis J121). The near-infrared light emitting diode 121d is fixed to a predetermined position of the case 121k in such a manner that the central axis is in agreement with the light emitting unit optical axis J121. The light emission side lens 121c is fixed to a predetermined position of the case 121k in such a manner that the optical axis is in agreement with the light emitting unit optical axis J121.

The light emitting unit optical axis J121 of the near-infrared light emitting unit 121 has an angle α to a normal line N1 of an irradiated surface P1. The near-infrared light emitting unit 121 projects near-infrared rays toward an intersection Q1 of the light emitting unit optical axis J121 and a normal line N1 of the irradiated surface P1 (light projection direction).

The near-infrared light emitting diode 121d emits near-infrared light beams with a wavelength of 700 nm to 3000 nm between visible light and infrared light. It is known that the near-infrared, light beam is absorbed by the hemoglobin, of blood. The near-infrared light emitting diode 121d is connected to a predetermined control portion and a power supply portion through a connection line 1211.

The reflected light receiving unit 123 has a light receiving side lens 123c, a photodiode array 123f, and a case 123k, The light receiving side lens 123c is an aspherical lens. The light receiving side lens 123c disperses reflected light beams of near-infrared rays projected by the near-infrared light emitting unit 121. The optical axis J123 of the light receiving side lens 123c has an angle β to the normal line direction N1 of the irradiated surface P1. The light receiving side lens 123c is fixed to a predetermined position of the case 123k.

The photodiode array 123f is one in which a plurality of photodiodes are arranged in a predetermined shape. The photodiode array 123f receives the reflected light beams dispersed by the light receiving side lens 123c with the front surface as a light receiving surface P3. The light receiving surface P3 of the photodiode array 123 has an angle γ to the light receiving unit optical axis J123. Thus, by disposing the photodiode array 123 in such a manner that the light receiving surface P3 inclines to the light receiving unit optical axis J123, a change in a substance in the normal line direction N1 of the incidence plane P1 can be obtained as a change in the illumination of the reflected light beams at the light receiving surface P3.

The photodiode array 123f is connected to an analysis circuit (not illustrated) and the like through the connection line 123l.

The light emitting unit optical axis J121 and the optical axis of the light receiving side lens 123c are present in the same plane. The light emitting unit optical axis J121 and the optical axis J123 of the light receiving side lens 123c are disposed in such a manner as to cross at a position with a distance d from the irradiated surface P1 to the inside of the body. The blood vessel position specifying device 111 detects whether or not a blood vessel is present at the intersection of the light emitting unit optical axis J121 and the optical axis J123C.

By selecting as appropriate, on the basis of the used conditions and components utilized, the angle α between the light emitting unit optical axis J121 of the near-infrared light emitting unit 121 and the normal line 111 of the irradiated surface P1, the angle β between the optical axis J123 of the light receiving side lens 123c and the normal line direction N1 of the irradiated surface P1, and the angle γ between the light receiving surface P3 of the photodiode array 123 and the light receiving unit optical axis J123, the blood vessel position can be more appropriately specified.

The analysis circuit is connected to the photodiode array 123f. The analysis circuit calculates the illumination in the depth direction of the normal line N1 of the irradiated surface P1 from light receiving results of the photodiode array 123f.

As illustrated in FIG. 5, the blood vessel position specifying device 111 further has another near-infrared light emitting unit 127. The configuration of the near-infrared light emitting unit 127 is the same as that of the near-infrared light emitting unit 121. The plane including the light emitting unit optical axis J127 of the near-infrared light emitting unit 127 and the normal line N1 of the irradiated surface P1 and the plane including the optical axis J123 of the light receiving side lens 123c and the normal line N1 of the irradiated surface P1 are disposed at 90°.

Thus, by disposing a plurality of near-infrared light emitting units at different positions to the reflected light receiving unit 123, the position of blood vessels can be specified irrespective of the arrangement state of blood vessels.

The case 125 has the near-infrared light emitting units 121 and 127 and the reflected light receiving unit 123 therein. The case 125 has the close contact surface 111s contacting the skin surface on the bottom. The case 125 further has the puncture aperture 111a in the close contact surface 111s. The surface where the puncture aperture 111a opens forms the irradiated surface P1. While the puncture aperture 111a allows near-infrared rays projected by the infrared light emitting units 121 and 127 to pass to the outside and allows only reflected light beams required for specifying the position of blood vessels to pass to the inside, the puncture aperture 111a prevents passage of unnecessary reflected light beams, such as a disturbance light beam.

The blood vessel position specifying device 111 starts to specify the position of blood vessels when a measurement starting button (not illustrated) provided at the case 125 is operated.

2. Principle for Specifying Blood Vessel Position and Simulation Results

Figure 6:
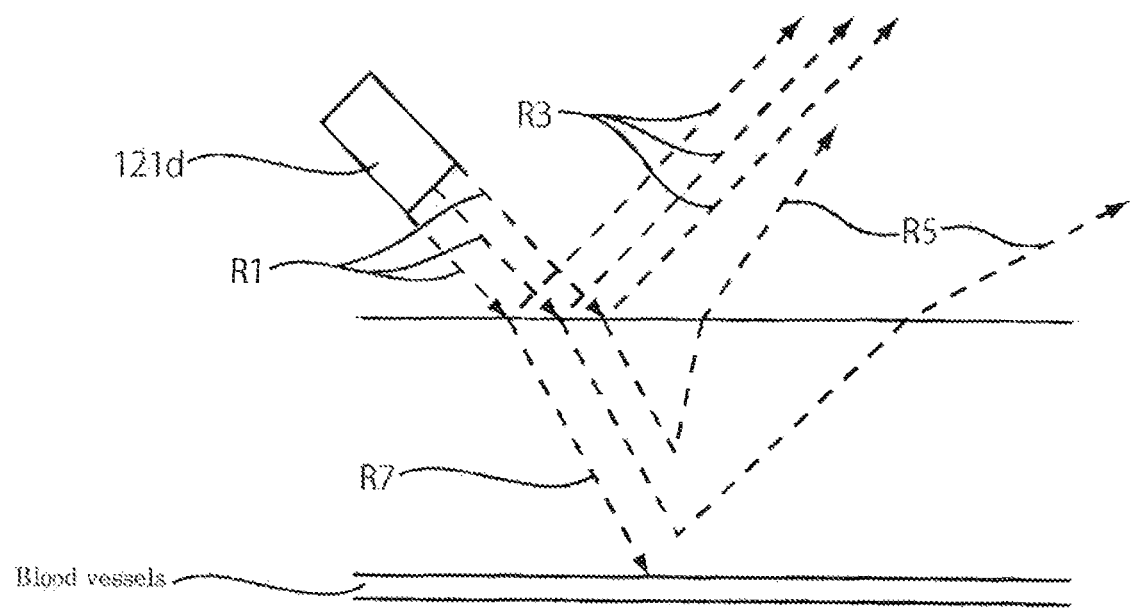
FIG. 6 is a view for explaining the principle of a method for specifying a blood vessel position.

The principle of the method for specifying a blood vessel position in the blood vessel position specifying device 111 is described with reference to FIG. 6. Near-infrared light beams R1 projected from the near-infrared light emitting diode 121d enter the skin through the light emission side lens 121c. Some of the near-infrared light beams R1 entering the skin become reflected light beams R3 on the skin surface. The other near-infrared light beams R1 enter the inside of the skin. The near-infrared light beams entering the inside of the skin repeats diffused reflection in the skin, and some light beams become reflected light beams R5 from the inside of the skin to go out to the outside from the skin surface.

A near-infrared light R7 which has reached a blood vessel among the near-infrared light beams entering the inside of the skin is absorbed by hemoglobin in the blood vessel.

Thus, the near-infrared light R7 absorbed into blood is not contained in the reflected light beams of the near-infrared light beams R1 projected by the near-infrared light emitting unit 121d. Therefore, by analyzing the reflected light beams of the near-infrared light beams R1, the position where blood is present, i.e., the position of blood vessels, can be specified.

FIGS. 7 to 10 show experimental results of specifying the position of a blood vessel by the blood vessel position specifying device 111. FIGS. 7 to 10 show the results of simulating, by a computer, a course of the near-infrared, light beams R1 projected by the near-infrared light emitting unit 121d.

Figure 7:
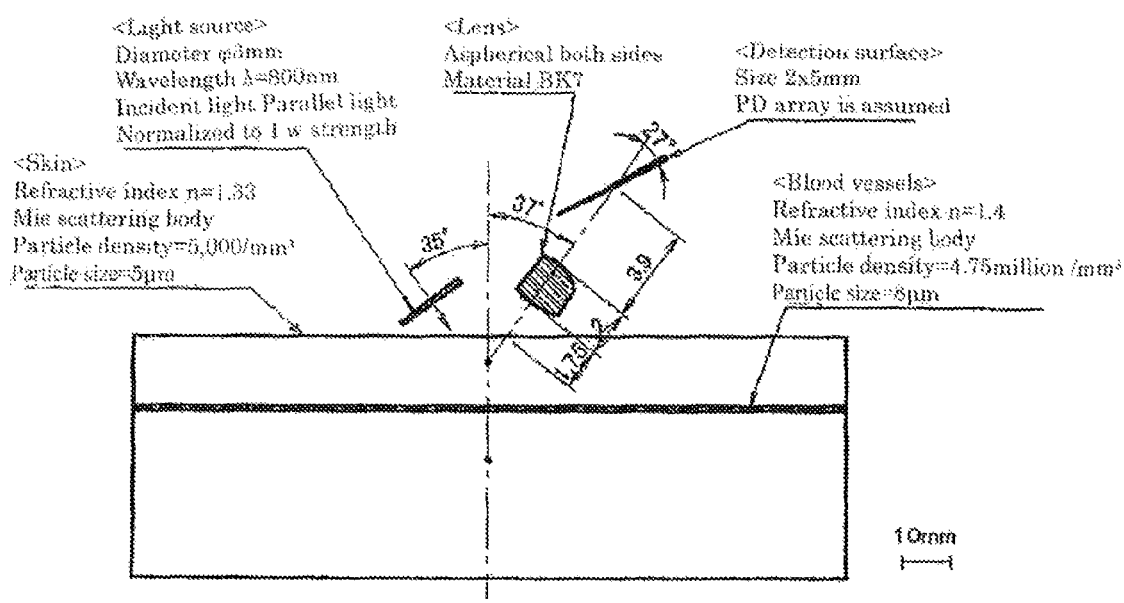
FIG. 7 is a view illustrating the conditions of simulation.

FIG. 7 shows conditions of a model built in the simulation. As illustrated in FIG. 7, in this simulation, a blood vessel is dealt as a Mie scattering body. Therefore, the near-infrared light beam which has reached the blood vessel is not absorbed into the blood in the blood vessel but is reflected by the blood vessel. Therefore, when the reflected light beams are actually analyzed by the blood vessel position specifying device 111, the intensity of the reflected light beams becomes lower depending on the depth where the blood vessel is present. However, in the simulation, the intensity of the reflected light beams becomes higher depending on the depth where the blood vessel is present.

Figure 8:
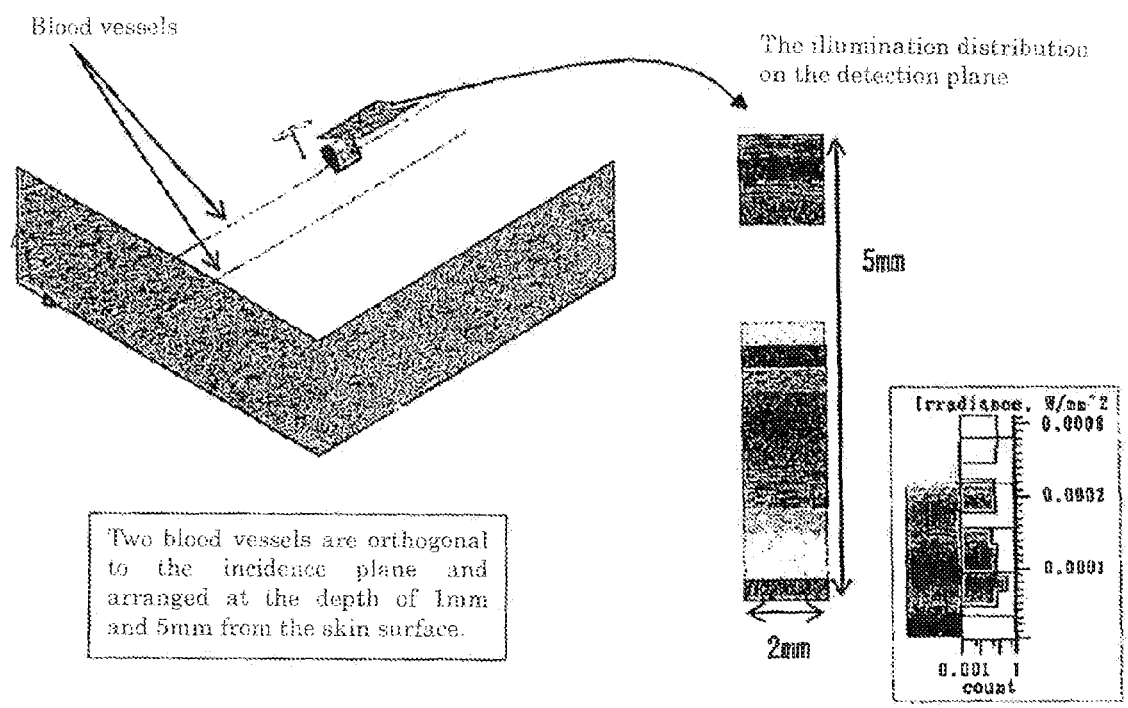
FIG. 8 is a view illustrating simulation results.

FIG. 8 illustrates the results of simulation in the case where two blood vessels are vertically present in parallel to each other under the skin orthogonal to the incidence plane of near-infrared light beams. The blood vessels are made to be present at depths of 1 mm and 5 mm from the skin surface, respectively, as illustrated in the left of FIG. 8.

In this case, as shown by the illumination distribution on the detection plane illustrated in the right of FIG. 8, the illumination becomes high around a depth of 1 mm and around a depth of 5 mm. More specifically, the blood vessel position specifying device 111 can specify that the blood vessels orthogonal to the incidence plane of near-infrared light beams are present at the depths of 1 mm and 5 mm from the skin surface.

Figure 9:
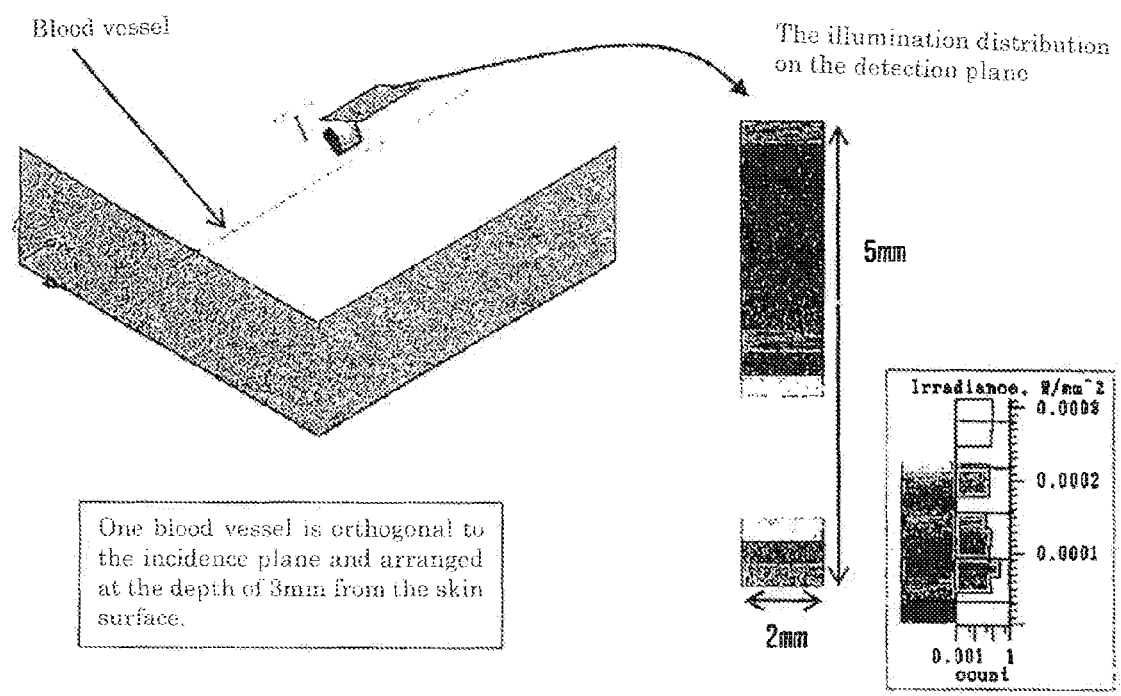
FIG. 9 is a view illustrating simulation results.

FIG. 9 shows the results of simulation in a case where one blood vessel is orthogonal to the incidence plane of near-infrared light beams under the skin. As shown in the left of FIG. 9, the blood vessel is made so be present at a depth of 3 mm from the skin surface.

In this case, as shown by the illumination distribution on the detection surface shown in the right of FIG. 9, the illumination becomes high around a depth of 3 mm. More specifically, the blood vessel position specifying device 111 can specify that the blood vessel orthogonal to the incidence plane of near-infrared light beams is present at a depth of 3 mm from the skin surface.

Figure 10:
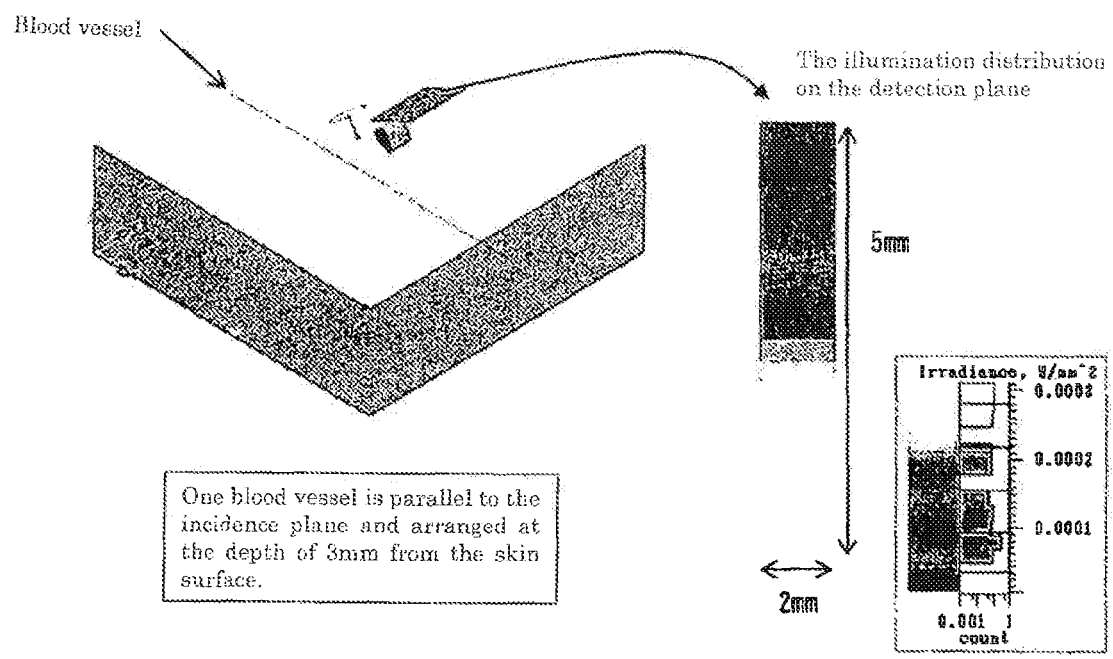
FIG. 10 is a view illustrating simulation results.
Figure 11:
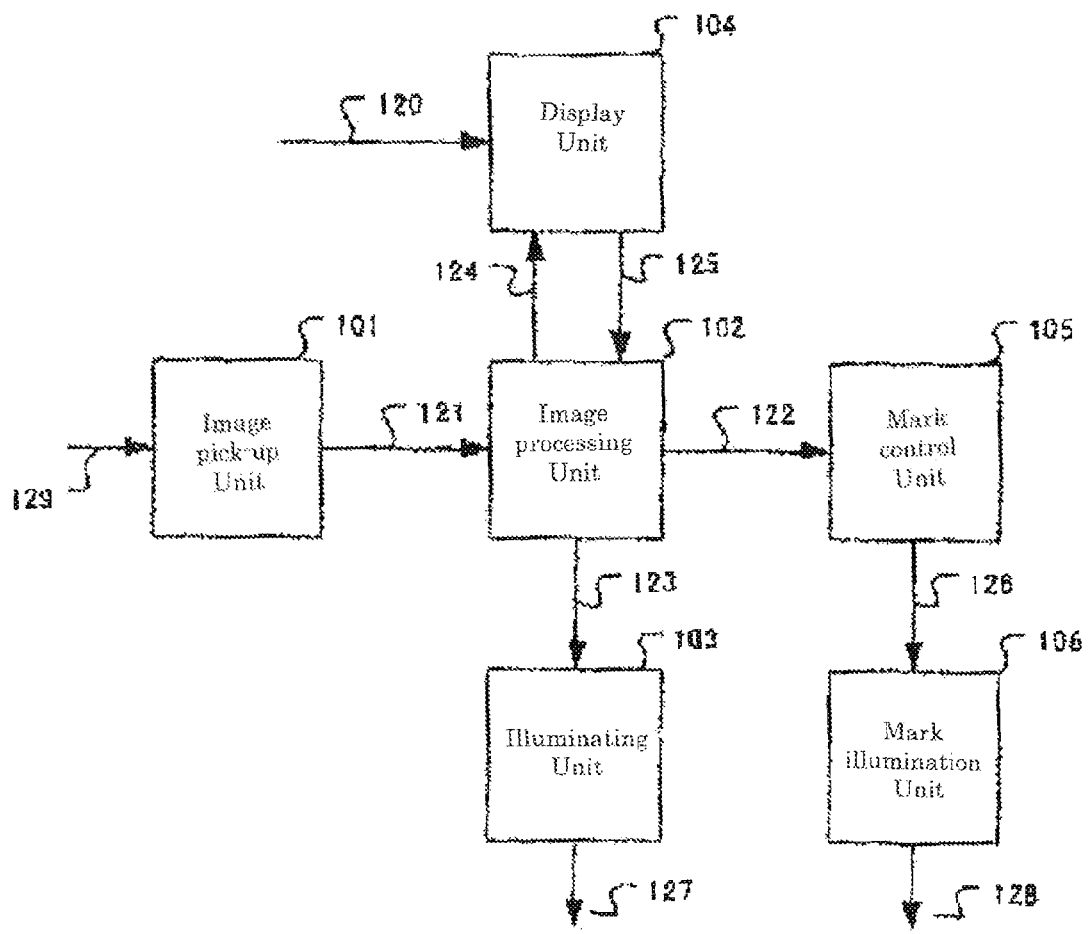
FIG. 11 is a view illustrating art example of a former blood vessel position specifying device.
Figure 12:
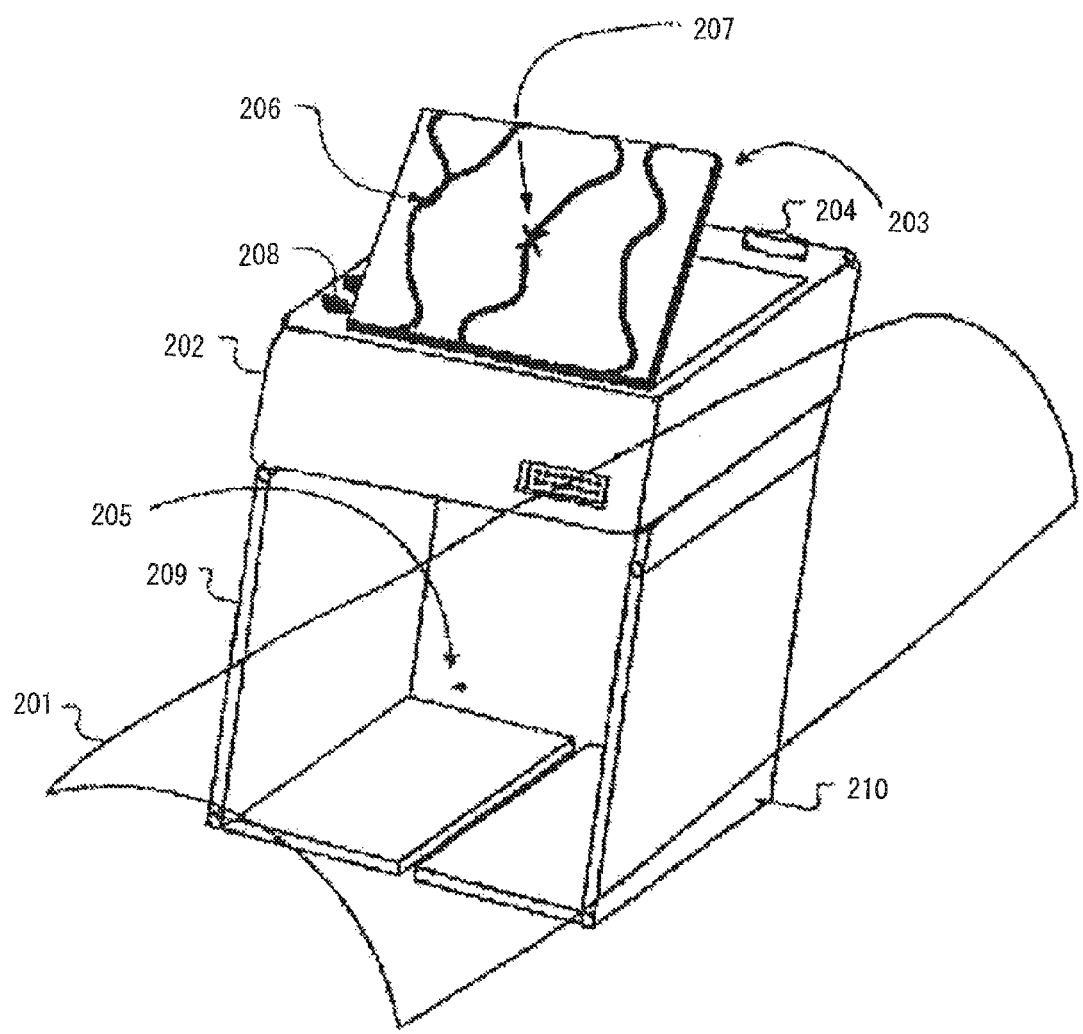
FIG. 12 is a view illustrating an example of a former blood vessel position specifying device.

FIG. 10 illustrates the results of simulation in a case where one blood vessel is present in parallel to the incidence plane of near-infrared light beams under the skin. As illustrated in the left of FIG. 10, the blood vessel is made to be present at a depth of 3 mm from the skin surface.

In this case, as shown by the illumination distribution on the detection surface shown in the right of FIG. 10, the illumination becomes higher at a position deeper than a depth of 3 mm. More specifically, the blood vessel position specifying device 111 specifies that she blood vessel present at a depth of 3 mm from the skin surface is present at a position deeper than a depth of 3 mm.

From she simulation results of FIG. 9 and FIG. 10, the blood vessel position specifying device 111a can more appropriately specify the depth in the case where a blood vessel is orthogonal to the incidence plane of near-infrared light beams rather than the case where a blood vessel is present in parallel to the incidence plane of near-infrared light beams. Therefore, in the blood vessel position specifying device 111, the two near-infrared light emitting units 121 are disposed in such a manner that the incidence planes of near-infrared light beams are orthogonal to each other. This allows more appropriate specification of the position of blood vessels.

Other Embodiments (1) Configuration of Blood Sampling Device 100:

In Embodiment 1 described above, the blood sampling device 100 is constituted by the blood vessel position specifying device 111 and the puncture device 113 which can be detached from catch other. However, the blood sampling device 100 may be integrally constituted by the blood vessel position specifying device 111 and the puncture device 113 which cannot be detached from each other.

(2) Arrangement of Near-Infrared Light Emitting Units

Although she two near-infrared light emitting units 121 and 127 are disposed at positions orthogonal to the reflected light receiving unit 123 in Embodiment 1 described above, the position is not limited to the example above insofar as the two near-infrared light emitting units 121 and 127 are disposed at different positions.

Alternatively, only one near-infrared light emitting unit 121 may be disposed in the blood sampling device 100. Furthermore, three or more near-infrared light emitting units may be disposed at different positions relative to the reflected light receiving unit 123.

(3) Light Receiving Side Lens 123c:

Although the light receiving side lens 123c is an aspherical lens in Embodiment 1 described, above, the lens is not limited to the example above insofar as the lens is a lens capable of dispersing a reflected light beam. For example, a spherical lens may be used.

(4) Photodiode Array 123f:

Although the photodiode array 123f is mentioned as one obtaining the brightness of a reflected light beam in Embodiment 1 described above, the photodiode array 123f is not limited to the example above insofar as the brightness of a reflected light beam can be obtained.

The blood vessel position specifying device according to the invention can be used for a blood sampling device which samples blood required in a blood test, for example.

DESCRIPTION OF REFERENCE NUMERALS

100 Blood sampling devise
111 Blood vessel position specifying device
121 Near-infrared light emitting unit
121d Hear-infrared light emitting diode
121c Light emission side lens
123 Reflected light receiving unit
123c Light receiving side lens
123f Photodiode array
113 Puncture device
113b Puncture needle

The invention claimed is:

1. A blood sampling device that samples blood from a blood vessel under a patient's skin, comprising:
   a light projection unit which has a light projection axis having a first predetermined angle to a normal line of a predetermined irradiated surface and which projects a near-infrared ray in a direction toward the normal line at or below said predetermined irradiated surface;
   a spectral lens which is located at the same side as a side where the light projection unit is located relative to the irradiated surface, which receives a reflected light beam of the near-infrared ray projected by the light projection unit, which disperses the reflected light beam, and which has an optical axis having a second predetermined angle to the normal line of the irradiated surface;
   a light receiving unit having a plurality of photodiodes, a set of multiple photodiodes among the plurality of photodiodes receiving a part of the dispersed reflected light beam, at least said set of the multiple photodiodes having an arrangement that facilitates determining depth position of the blood vessel, said arrangement being along a photodiode line within a plane including said normal line, said optical axis, said photodiode line being inclined relative to said optical axis so as to be neither parallel nor perpendicular to said optical axis;
   a processing unit which calculates said depth position of the blood vessel in a direction of the normal line, based on a position of a photodiode, among the plurality of photodiodes, whose illuminance is smaller than a threshold within an illuminance distribution of the dispersed reflected light beam received by the plurality of photodiodes;
   a contact surface configured to make contact with said skin and having a puncture aperture; and
   a needle projecting unit comprising a puncture button and a needle, the needle being for use in blood sampling, the needle projecting unit configured to project the needle in response to actuation of said puncture button, the needle projecting unit automatically projecting said needle from a position in which the needle is arranged inside said blood sampling device to a position in which at least a portion of the needle projects outside the blood sampling device through said puncture aperture with aiming to the depth position of the blood vessel calculated based on position of said photodiode, among the set of multiple photodiodes, receiving the dispersed reflected light beam from the blood vessel, so as to project a tip of the needle into the blood vessel; and
   wherein the intersection of the light projection axis and the optical axis of the spectral lens is located at a side opposite to the side where the light projection unit and the spectral lens are located relative to the irradiated surface;

wherein the light projection unit irradiates a light beam of the near-infrared ray on the irradiated surface through the puncture aperture; and wherein the spectral lens is configured to disperse the reflected light beam through the puncture aperture.

2. The blood sampling device according to claim 1, wherein the light receiving unit is disposed in such a manner that the light receiving surface inclines to the optical axis.

3. The blood sampling device according to claim 1, wherein the light projection axis of the light projection unit and the optical axis of the spectral lens are present in the same plane.

4. The blood sampling device according to claim 1, wherein a plane including the light projection axis of the light projection unit and the normal line of the irradiated surface and a plane including the optical axis of the spectral lens and the normal line of the irradiated surface are disposed at a predetermined angle.

5. The blood sampling device according to claim 4, wherein the plane including the light projection axis of the light projection unit and the normal line of the irradiated surface and the plane including the optical axis of the spectral lens and the normal line of the irradiated surface are disposed at 90.

6. The blood sampling device according to claim 1, wherein the spectral lens is an aspherical lens.

7. A blood sampling method for sampling blood from a blood vessel present under skin using a blood sampling device comprising a light projection unit, a spectral lens, a light receiving unit having a plurality of photodiodes, a processing unit, a puncture button, a contact surface, and a needle projecting unit the blood sampling method, comprising:

projecting from the light projection unit a near-infrared ray, while defining a direction having a first predetermined angle to a normal line direction of a predetermined irradiated surface as a light projection direction, the near-infrared ray being projected through a puncture aperture configured on said contact surface, the contact surface configured to be in contact with the skin;

dispersing a reflected light beam of the near-infrared ray projected by the light projection unit using the spectral lens located at the same side of the blood sampling device as a side where the light projection unit is located relative to the irradiated surface and having a second predetermined angle to the normal line direction of the irradiated surface as an optical axis direction and received through the puncture aperture;

receiving a part of the dispersed reflected light beam at a set of multiple photodiodes among the plurality of photodiodes, at least said set of the multiple photodiodes having an arrangement that facilitates determining depth position of the blood vessel, said arrangement being along a photodiode line within a plane including the normal line direction, the light projection direction, and the optical axis direction, said photodiode line being inclined relative to said optical axis direction so as to be neither parallel nor perpendicular to said optical axis;

calculating with the processing unit a depth position of the blood vessel in a direction of the normal line direction, based on a position of a photodiode, among the set of multiple photodiodes, whose illuminance is smaller than a threshold within an illuminance distribution of the dispersed reflected light beam received by the set of multiple photodiodes; and projecting, automatically by the needle projecting unit, a needle for use in blood sampling through said puncture aperture with aiming at the position of the blood vessel calculated by the processing unit in response to the puncture button being pushed.

8. The blood sampling device of claim 1, wherein the contact surface is disposed so that said predetermined irradiated surface of said skin is exposed within said puncture aperture to said projected near-infrared ray light.

9. The blood sampling device of claim 1, further comprising a case having said contact surface and housing said light projection unit, spectral lens, and photodiode array.

10. The blood sampling device of claim 1, wherein the photodiodes among said set of photodiodes are configured so that the nearer each one photodiode of the set of photodiodes is to the normal line, the nearer said one photodiode is to the spectral lens, and the farther said one photodiode is from the normal line, the farther said one photodiode is from the spectral lens.

* * * * *

UNITED STATES PATENT AND TRADEMARK OFFICE
CERTIFICATE OF CORRECTION

PATENT NO. : 9,713,426 B2
APPLICATION NO. : 13/637221
DATED : July 25, 2017
INVENTOR(S) : Konishi et al.

Page 1 of 1

It is certified that error appears in the above-identified patent and that said Letters Patent is hereby corrected as shown below:

On the Title Page

At item (73), change "(73) Assignee: Nipro Corporation (JP)" to -- (73) Assignee: Nipro Corporation (JP); The Ritsumeikan Trust (JP) --

Signed and Sealed this
Tenth Day of July, 2018

Andrei Iancu
*Director of the United States Patent and Trademark Office*